US012178728B2

(12) United States Patent
Gagner et al.

(10) Patent No.: US 12,178,728 B2
(45) Date of Patent: Dec. 31, 2024

(54) ACTIVABLE BOUGIE FOR PERFORMING GASTROPLASTY

(71) Applicant: Ballast Medical Inc., Montreal (CA)

(72) Inventors: Michel Gagner, Montreal (CA); David J. Blaeser, Brooklyn Park, MN (US); Dale A. Spencer, Wayzata, MN (US)

(73) Assignee: BALLAST MEDICAL INC., Montreal (CA)

( * ) Notice: Subject to any disclaimer, the term of this patent is extended or adjusted under 35 U.S.C. 154(b) by 287 days.

(21) Appl. No.: 17/973,023

(22) Filed: Oct. 25, 2022

(65) Prior Publication Data

US 2023/0040585 A1 Feb. 9, 2023

Related U.S. Application Data

(63) Continuation of application No. 16/575,682, filed on Sep. 19, 2019, now Pat. No. 11,510,799, which is a
(Continued)

(51) Int. Cl.
*A61F 5/00* (2006.01)
*A61B 17/072* (2006.01)
(Continued)

(52) U.S. Cl.
CPC ...... *A61F 5/0076* (2013.01); *A61B 17/07207* (2013.01); *A61B 17/115* (2013.01); *A61F 5/0083* (2013.01); *A61B 2017/00119* (2013.01); *A61B 2017/00278* (2013.01); *A61B 2017/00818* (2013.01); *A61B 2017/00827* (2013.01)

(58) Field of Classification Search
CPC . A61B 17/00; A61B 17/07207; A61B 17/115; A61B 2017/00119; A61B 2017/00278; A61B 2017/00818; A61B 2017/00827; A61F 5/00; A61F 5/0083
See application file for complete search history.

(56) References Cited

U.S. PATENT DOCUMENTS 5,676,674 A 10/1997 Bolanos et al.
5,718,666 A 2/1998 Alarcon
(Continued)

FOREIGN PATENT DOCUMENTS

WO 200224080 A2 3/2002
WO 2002028289 A1 4/2002
(Continued)

OTHER PUBLICATIONS

WIPO, U.S. International Search Authority, International Search Report and Written Opinion mailed Mar. 12, 2009 in International Patent Application No. PCT/US2009/032741, 8 pages.
(Continued)

*Primary Examiner* — Benjamin J Klein
(74) *Attorney, Agent, or Firm* — Thomas | Horstemeyer, LLP

(57) ABSTRACT

A gastroplasty method involves a staple line that terminates prior to reaching the gastroesophageal junction such that the bypassed portion of the stomach does not require resection. Additionally, bougies are taught that assist a physician in following the improved staple line of the present invention.

20 Claims, 7 Drawing Sheets

Related U.S. Application Data continuation of application No. 15/369,035, filed on Dec. 5, 2016, now Pat. No. 10,433,997, which is a continuation of application No. 14/174,802, filed on Feb. 6, 2014, now Pat. No. 9,549,737, which is a continuation of application No. 12/865,709, filed as application No. PCT/US2009/032741 on Jan. 30, 2009, now Pat. No. 8,663,149.

(60) Provisional application No. 61/025,619, filed on Feb. 1, 2008.

(51) Int. Cl.
  *A61B 17/115* (2006.01)
  *A61B 17/00* (2006.01)

(56) References Cited

U.S. PATENT DOCUMENTS

| | | | |
|---|---|---|---|
| 6,773,441 | B1 | 8/2004 | Laufer et al. |
| 7,837,698 | B2 * | 11/2010 | DeVries ............ A61B 17/06109 606/139 |
| 8,663,149 | B2 | 3/2014 | Gagner et al. |
| 9,549,737 | B2 | 1/2017 | Gagner et al. |
| 10,433,997 | B2 | 10/2019 | Gagner |
| 2002/0082621 | A1 * | 6/2002 | Schurr ................ A61B 17/068 606/151 |
| 2003/0216754 | A1 | 11/2003 | Kraemer et al. |
| 2003/0220657 | A1 * | 11/2003 | Adams ............... A61B 17/0643 606/139 |
| 2003/0236536 | A1 | 12/2003 | Grigoryants et al. |
| 2005/0251158 | A1 * | 11/2005 | Saadat ............... A61B 17/1285 606/153 |
| 2007/0038232 | A1 * | 2/2007 | Kraemer ............ A61B 17/1114 606/153 |
| 2007/0112363 | A1 * | 5/2007 | Adams ............... A61B 17/0487 606/153 |
| 2007/0167960 | A1 * | 7/2007 | Roth .................... A61B 17/072 606/153 |
| 2008/0262300 | A1 | 10/2008 | Ewers et al. |
| 2010/0217291 | A1 * | 8/2010 | Baker ................... A61B 17/12 606/153 |
| 2011/0213390 | A1 | 9/2011 | Kraemer et al. |

FOREIGN PATENT DOCUMENTS

| | | |
|---|---|---|
| WO | 2002094105 A2 | 11/2002 |
| WO | 2006023764 A2 | 3/2006 |
| WO | 2006060549 A2 | 6/2006 |

OTHER PUBLICATIONS

USPTO, Notice of Allowance mailed Oct. 11, 2013 in U.S. Appl. No. 12/865,709, 12 pages.
USPTO, Office Action mailed Jul. 2, 2013 in U.S. Appl. No. 12/865,709, 10 pages.
IP Australia, Examination Report dated Apr. 26, 2013 in Australian Patent Application No. 2009-208954, 3 pages.
USPTO, Final Office Action mailed Feb. 26, 2013 in U.S. Appl. No. 12/865,709, 15 pages.
USPTO, Office Action mailed Oct. 9, 2012 in U.S. Appl. No. 12/865,709, 11 pages.

* cited by examiner

ACTIVABLE BOUGIE FOR PERFORMING GASTROPLASTY

PRIORITY CLAIM TO RELATED APPLICATIONS

This application is a continuation of and claims priority to U.S. patent application Ser. No. 16/575,682, entitled Bougie Including a Light Source for Performing Gastroplasty, filed Sep. 19, 2019, which application is a continuation of and claims priority to U.S. patent application Ser. No. 15/369,035, entitled Bougie Including a Light Source for Performing Gastroplasty, filed Dec. 5, 2016, now U.S. Pat. No. 10,433,997, issued Oct. 8, 2019, which application is a continuation of and claims priority to U.S. patent application Ser. No. 14/174,802, entitled Method and "Devices for Performing Gastroplasty, filed Feb. 6, 2014, now U.S. Pat. No. 9,549,737, issued Jan. 1, 2017, which application is a continuation of and claims priority to U.S. patent application Ser. No. 12/865,709, filed Feb. 28, 2011, entitled Methods And Devices For Performing Gastroplasty, now U.S. Pat. No. 8,663,149, issued Mar. 4, 2014, which is the U.S. National Phase of and claims priority to International Patent Application No. PCT/US2009/032741, International Filing Date Jan. 30, 2009, entitled Methods And Devices For Performing Gastroplasty, which claims priority to U.S. Provisional Patent Application Ser. No. 61/025,619, filed Feb. 1, 2008 by Gagner et al., entitled Methods And Devices For Performing Gastroplasty, the contents of all of which are incorporated herein in their entireties.

BACKGROUND OF THE INVENTION

The present invention relates generally to improved methods and devices for anchoring a gastroenterologic sleeve within the stomach without reliance on sutures, staples, or other mechanisms that puncture the stomach wall. In addition to leaving the stomach walls free of punctures, the anchoring system of the present invention prevents movement of the sleeve in both directions, thereby preventing the sleeve from being passed through the digestive system but also from refluxing up the esophagus.

According to the Center for Disease Control (CDC), sixty six percent of American are overweight, and thirty two percent are obese, presenting an overwhelming health problem. From an economic standpoint, it is estimated that more than 100 billion dollars are spent on obesity and treating its major co-morbidities. This figure does not include psychological and social costs. Many health care experts consider obesity the largest health problem facing westernized societies and considered obesity an epidemic. From a medical standpoint, obesity is the primary risk factor for type 2 diabetes and obstructive sleep apnea. It increases the chances for heart disease, pulmonary disease, infertility, osteoarthritis, cholecystitis and several major cancers, including breast and colon cancers. Despite these alarming facts, treatment options for obesity remain limited.

Treatment options include dietary modification, very low-calorie liquid diets, pharmaceutical agents, counseling, exercise programs and surgery. Diet and exercise plans often fail because most individuals do not have the discipline to adhere to such plans. When diet and exercise fail, many try dietary supplements and drugs or other ingestible preparations promoted as being capable of suppressing appetite or inducing satiety. In general, these techniques for treating compulsive overeating/obesity have tended to produce only a temporary effect. The individual usually becomes discouraged and/or depressed after the initial rate of weight loss plateaus and further weight loss becomes harder to achieve. The individual then typically reverts to the previous behavior of compulsive overeating.

Surgical procedures that restrict the size of the stomach and/or bypass parts of the intestine are the only remedies that provide lasting weight loss for the majority of morbidly obese individuals. Surgical procedures for morbid obesity are becoming more common based on long-term successful weight loss result.

Bariatric surgery is a treatment for morbid obesity that involves alteration of a patient's digestive tract to encourage weight loss and to help maintain normal weight. Known bariatric surgery procedures include jejuno-ileal bypass, jejuno-colic shunt, biliopancreatic diversion, gastric bypass, Roux-en-Y gastric bypass, gastroplasty, gastric banding, vertical banded gastroplasty, and silastic ring gastroplasty. A more complete history of bariatric surgery can be found on the website of the American Society for Bariatric Surgery at http://www.asbs.org, the contents of which are incorporated by reference herein in their entirety.

Advances in laparoscopic surgery have allowed physicians to perform operations that previously required an invasive and painful access incision to be made. For example, in the case of a sleeve gastrectomy, a surgeon would make an abdominal incision, typically 5 cm or more in length, which provided access to the abdominal cavity. The surgeon would then suture the stomach together, forming a stoma, using a bougie as a guide along the lesser curvature of the stomach. A bougie is a relatively simple, solid tube inserted into the stomach via the esophagus. The surgeon sutures the stomach shut around the bougie, such that the stoma formed matches the size and the narrow, tubular shape of the bougie.

Conducting this surgery laparoscopically minimizes trauma to the patient because the large abdominal incision is avoided. In female patients, the vagina may be used as an entry point, further minimizing trauma to the abdomen. Recovery time and the chances for infection are greatly reduced using laparoscopic surgery.

However, laparoscopic surgery adds certain complications. In the case of a sleeve gastrectomy, because the suture line extends along the entire length of the stomach, a majority of the stomach is completely isolated from the digestive path. This stomach portion must be removed from the body. Hence, a sleeve gastrectomy begins with the transection of the short gastric arteries to the left diaphragmatic crus. Care must be taken to avoid damaging the spleen or its vessels. This makes removal of the unused stomach portion the most complicated aspect of a sleeve gastrectomy, whether performed laparoscopically or surgically. Laparoscopically transecting these arteries and removing the unused stomach portion is significantly more difficult than doing so surgically. In the case of a vaginal-entry laparoscopy, removing the resected stomach portion through the entry opening in the vagina can be particularly difficult, especially considering that the typical patient undergoing such a surgery as a significantly enlarged stomach.

There is an apparent need for a device and method of performing a sleeve gastrectomy obviates the need for removing any portion of the stomach. If the entire stomach can be left in place, patient recovery time, procedural complexity, and patient morbidity rates will be greatly reduced.

SUMMARY OF THE INVENTION

The present invention provides a device and method for performing a sleeve gastrectomy while obviating the need to resect the bypassed portion of the stomach. The need for resection is obviated by ending suture line a relatively short distance from the gastroesophageal junction. By leaving this small opening between the stoma and the bypassed portion of the stomach, the bypassed portion can remain in place without complication, despite the absence of food.

To prevent food from passing through this opening, the suture line is angled away from the gastroesophageal junction near the top of the stomach. This is effected by the use of an embodiment of a bougie of the present invention. The bougie includes an extension that, when opened, gives the bougie a Y shape. The resulting stoma has an open top near the gastroesophageal junction but, due to the extension, it is funnel-shaped and thus directs food into the stoma instead of the bypassed stomach. Several embodiments of bougies are described herein.

DETAILED DESCRIPTION OF THE INVENTION

Figure 6:
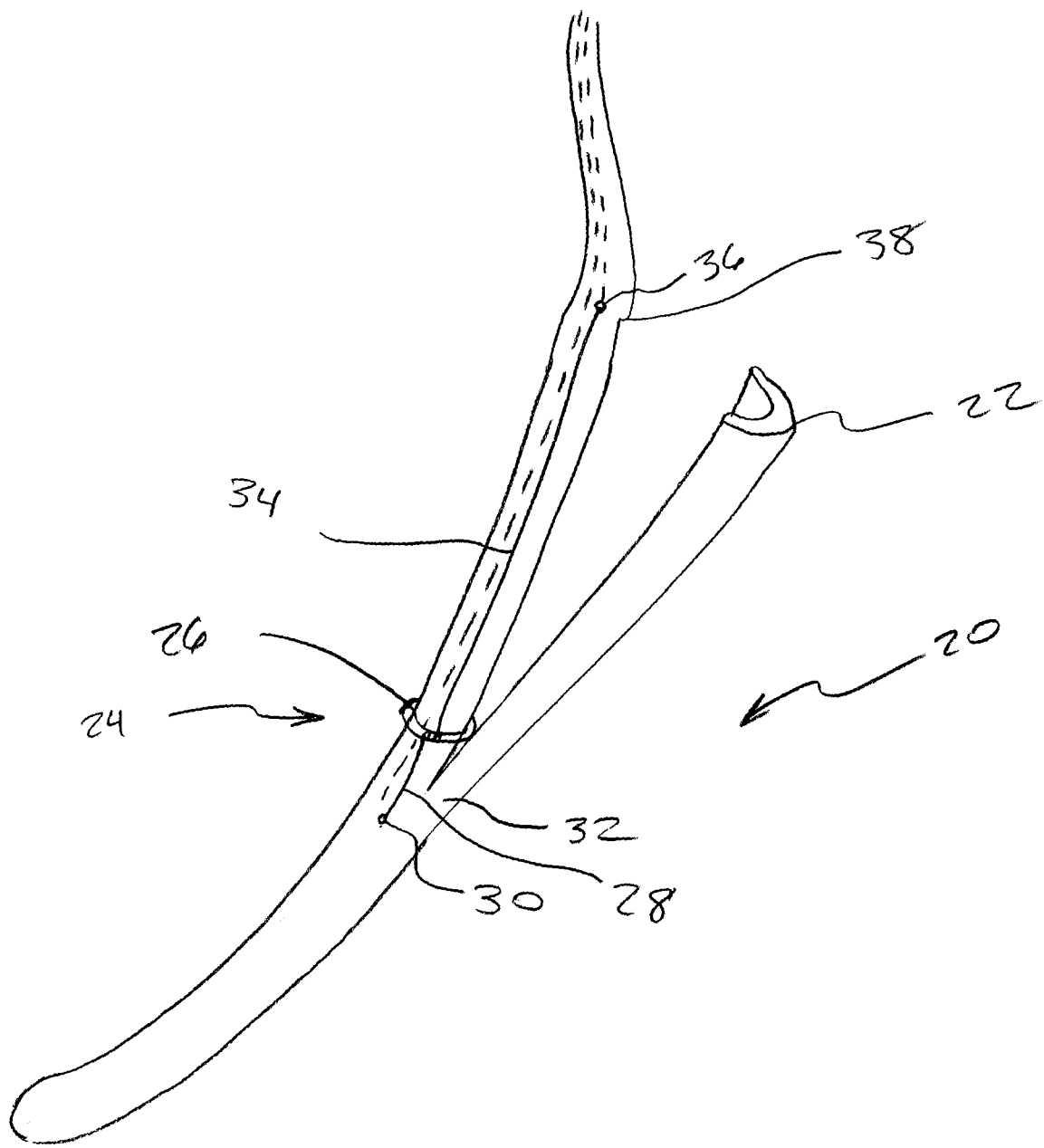
FIG. 6 is a perspective view of an embodiment of a device of the present invention; and, FIG. 7 is a perspective view of an embodiment of a device of the present invention.
Figure 7:
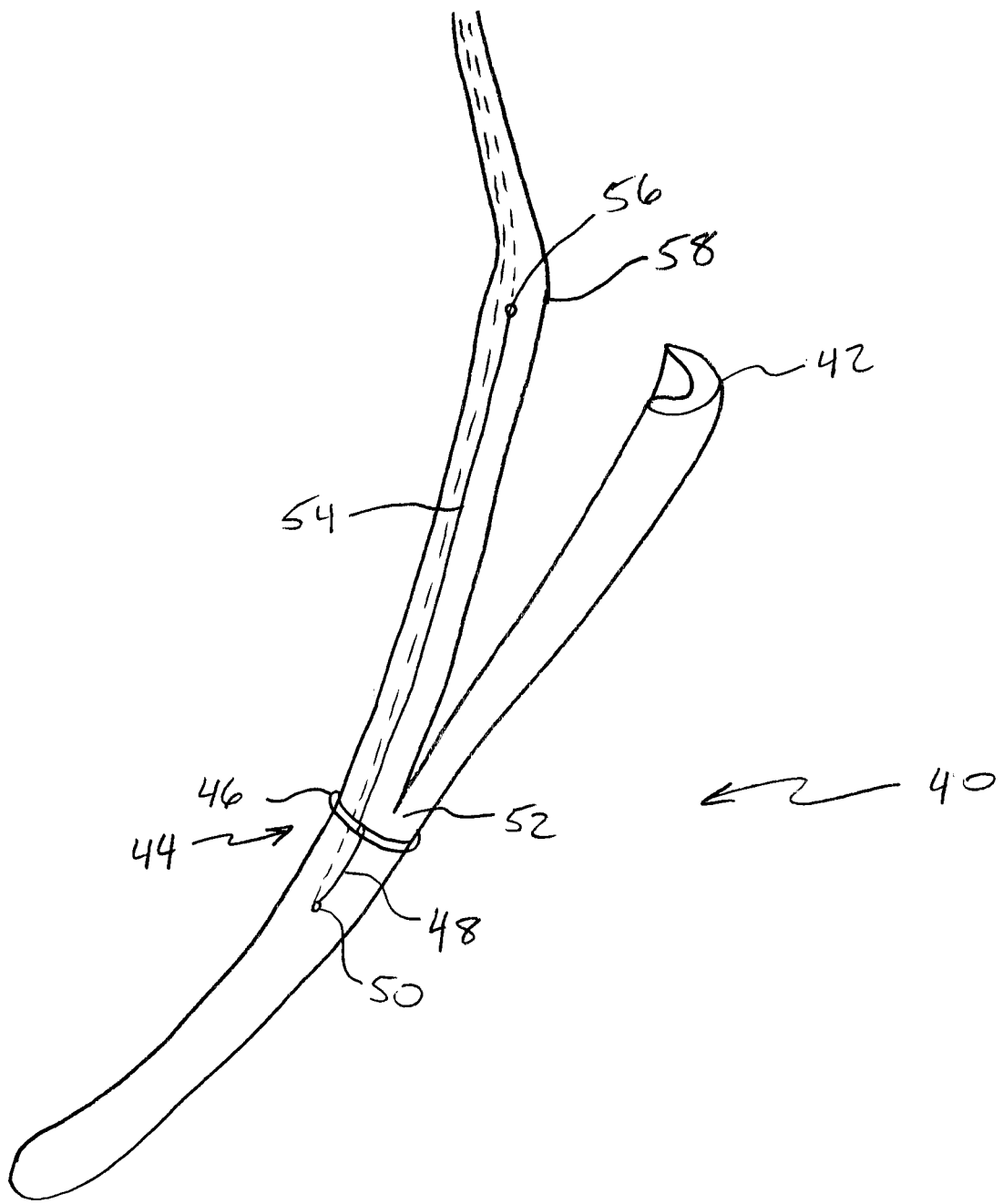

The present invention includes a method and devices for performing a gastroplasty procedure. FIGS. 1-5 show a series of diagrams detailing the various steps of the method. FIGS. 6-7 depict several embodiments of various devices. By explaining the method first, the various embodiments of devices will be more easily understood.

The gastroplasty method of the present invention begins by introducing a bougie 10 into the stomach A via the esophagus B. The bougie 10 is preferably shaped to follow the lesser curve C of the stomach A.

Figure 1:
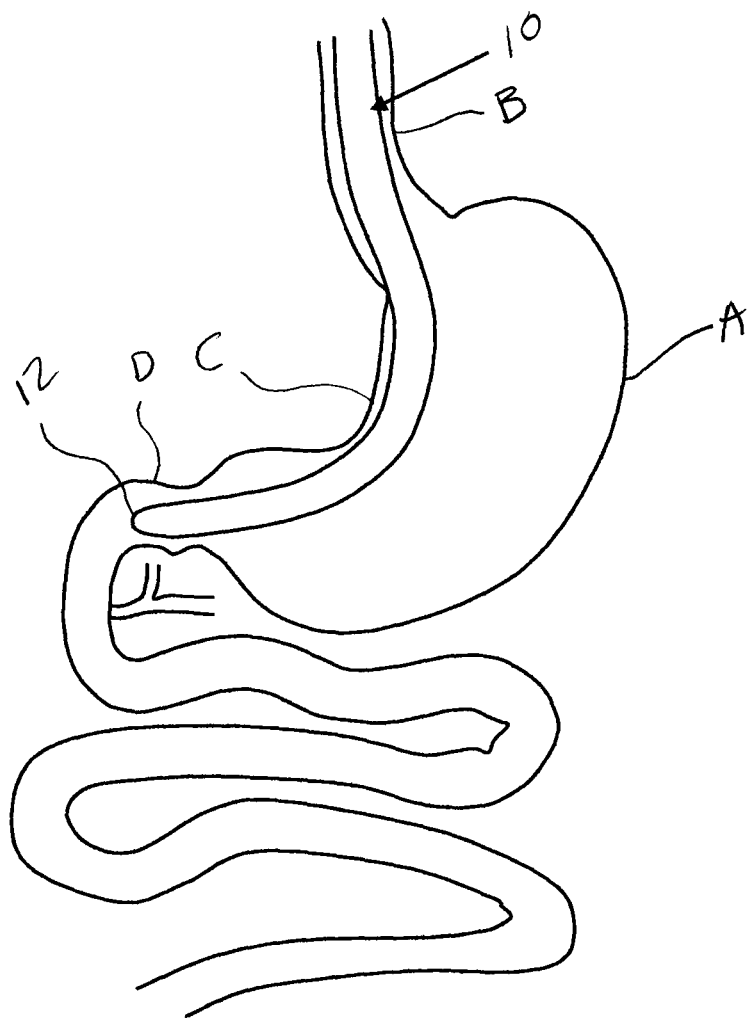
FIG. 1 is an elevation of a first step of the method of the present invention.
Figure 2:
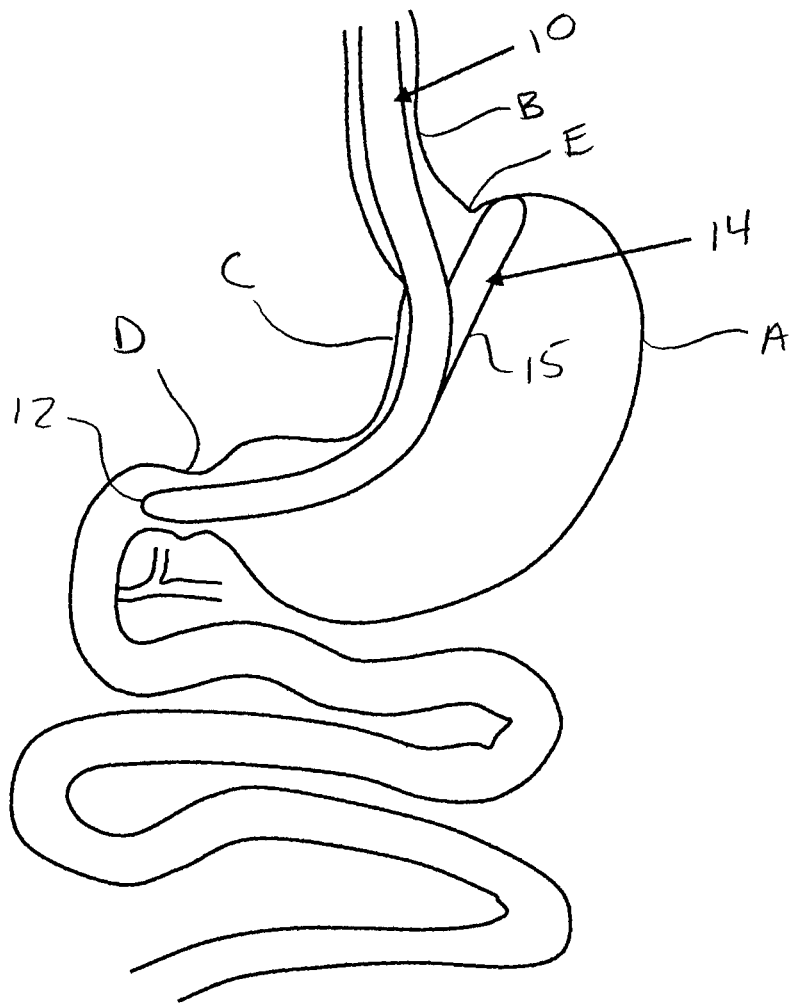
FIG. 2 is an elevation of a second step of the method of the present invention.

Once the bougie 10 is in place such that its distal end 12 is near the gastro-duodenal junction D, an extension 14 of the bougie 10 is splayed open as depicted in FIG. 2. The extension 14 opens enough such that the inner edge 15 of the bougie 10, opposite the lesser curve C, extends away from the gastroesophageal junction E.

Figure 3:
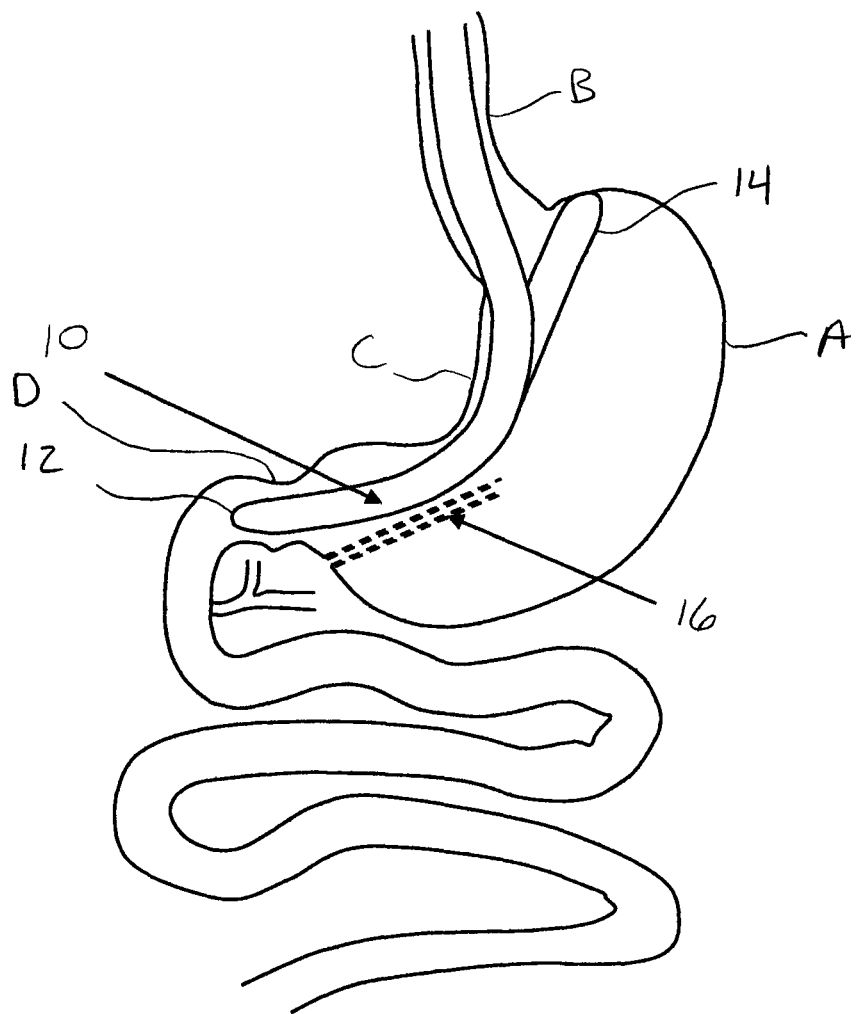
FIG. 3 is an elevation of a third step of the method of the present invention.
Figure 4:
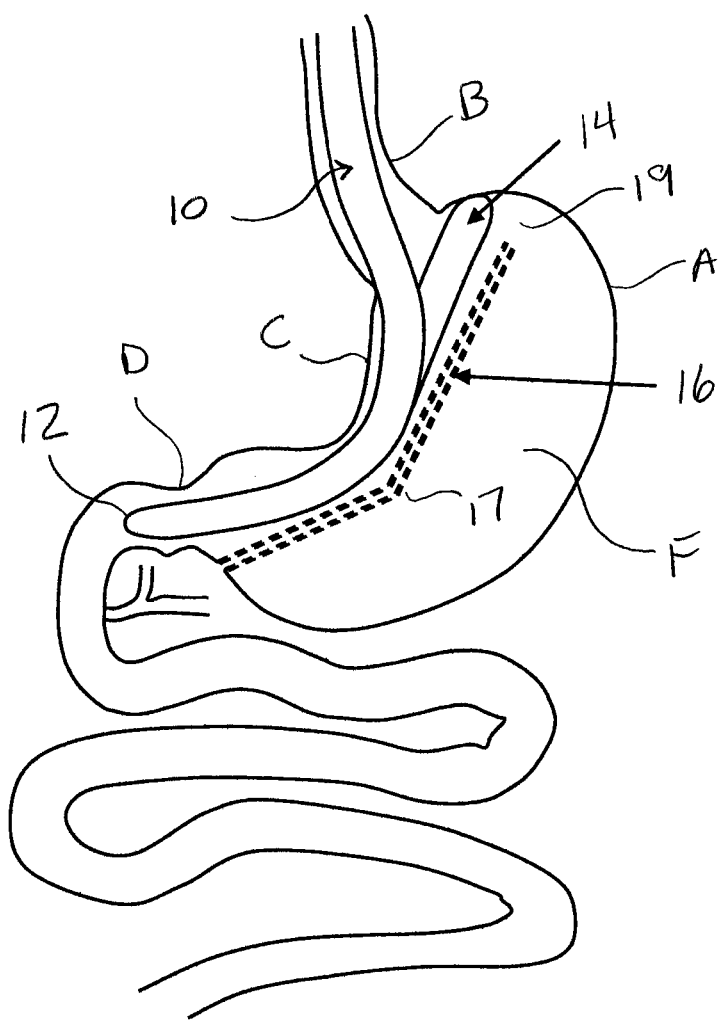
FIG. 4 is an elevation of a fourth step of the method of the present invention.

Next, as seen in FIG. 3, a staple line 16 is followed along the inner edge 15 of the bougie 10 beginning at the bottom of the stomach A and working up toward the esophagus B. Optionally, suction may be applied to the stomach A, such that the stomach A collapses and is sucked against the bougie 10, making the bougie 10 and the desired staple line 16 easier to visualize and follow. Additionally or alternatively, the bougie 10 may include a light source visible through the wall of the stomach A, thereby improving visibility. As seen in FIG. 4, the suture line 16 will likely include a bend 17 or angle that follows the bougie 10.

Figure 5:
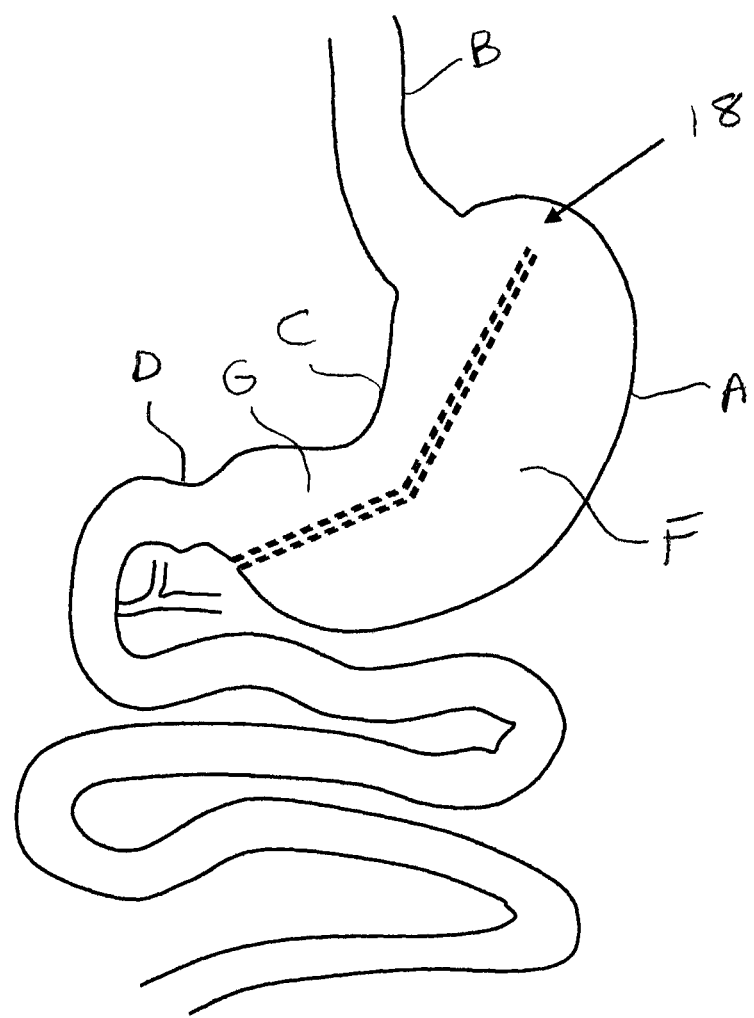
FIG. 5 is an elevation of stomach having undergone the method of the present invention.

FIG. 5 shows that the suture line 16 ends prior to reaching the top of the stomach. A space 19 is left that allows some communication between the bypassed portion of the stomach F and the newly formed stoma G. After the staple line 16 is complete, the extension 14 is closed against the bougie 10 and the bougie 10 is retracted through the esophagus B.

Turning now to FIGS. 6-7, there are shown several embodiments of bougies suitable for use with the method of the present invention.

FIG. 6 shows a bougie 20 with an extension 22 and an activation device 24. The extension 22 is biased shut but is flexible enough to be held open using the activation device 24.

The activation device 24 includes a sliding ring 26 that passes around the outside of the bougie 20 but not including the extension 22. An extending wire 28 passes through an internal lumen of the bougie 20 and exits the bougie through a port 30 located distally of a distal end 32 of the extension 22. The extending wire 28 is then routed proximally and attached to the sliding ring 26. Preferably, though not shown in the figures, a second extending wire is similarly routed on an opposite side of the bougie 20 such that when pulled, and equal force is applied to both sides of the ring 26, thereby preventing the ring from hanging up on the bougie 20.

One or preferably two (one shown) retraction wires 34 are also routed through an internal lumen of the bougie, exiting at a port 36 located proximally of the proximal end 38 of the bougie 20. The retraction wires 34 are also connected to the sliding ring 26.

In operation, the bougie 20 is placed as desired in the stomach and the extension 22 is splayed open by pulling on the extending wire or wires 28, thereby pulling the ring 26 down in a distal direction. The ring 26 is wedged between the extension 22 and the rest of the bougie 20. The further the ring 26 is pulled toward the junction between the extension 22 and the bougie 20, the greater the angle between the two becomes.

When the extension 22 is splayed a desired amount, the stapling step of the procedure is accomplished. To remove the bougie 20, the retraction wire or wires 34 are pulled, thereby pulling the sliding ring 26 in a proximal direction. The resilient nature of the extension 22 brings it flush against the bougie 20 and the bougie 20 may be removed.

Turning now to FIG. 7, there is shown another embodiment of a bougie 40 of the present invention with an extension 42 and an activation device 44. The extension 42 is biased open but is flexible enough to be held closed using the activation device 44.

The activation device 44 includes a sliding ring 46 that passes around the outside of the bougie 40, including the extension 42. An extending wire 48 passes through an internal lumen of the bougie 40 and exits the bougie through a port 50 located near or distally of a distal end 52 of the extension 42. The extending wire 48 is then routed proximally and attached to the sliding ring 46. Preferably, though not shown in the figures, a second extending wire is similarly routed on an opposite side of the bougie 40 such that when pulled, and equal force is applied to both sides of the ring 46, thereby preventing the ring from hanging up on the bougie 40.

One or preferably two (one shown) retraction wires 54 are also routed through an internal lumen of the bougie, exiting at a port 56 located proximally of the proximal end 58 of the bougie 40. The retraction wires 54 are also connected to the sliding ring 46.

In operation, the bougie 40 is placed as desired in the stomach and the extension 42 is splayed open by pulling on the extending wire or wires 48, thereby pulling the ring 26 down in a distal direction. The ring 46 releases the extension 42 and the biased-open extension is free to splay. Depending on the how over-sized the ring 46 is compared to the bougie, the further the ring 46 is pulled toward the junction between the extension 42 and the bougie 40, the greater the angle between the two becomes.

When the extension 42 is splayed a desired amount, the stapling step of the procedure is accomplished. To remove the bougie 40, the retraction wire or wires 54 are pulled, thereby pulling the sliding ring 46 in a proximal direction. The ring 46 collapses the extension 42 flush against the bougie 40 and the bougie 40 may be removed. Preferably the port 56 is located such that the ring 46 cannot be drawn past the proximal end of the extension 42, such that an accidental splaying of the extension 42 during withdrawal is not possible.

Although the invention has been described in terms of particular embodiments and applications, one of ordinary skill in the art, in light of this teaching, can generate additional embodiments and modifications without departing from the spirit of or exceeding the scope of the claimed invention. For example, one skilled in the art will realize several embodiments bougies that include an extension and various was to deploy and retract this extension. Just a few, non-limiting examples of other devices include, but are not limited to, screw-activated devices, balloon activated devices, ratcheting devices, and the like. Accordingly, it is to be understood that the drawings and descriptions herein are proffered by way of example to facilitate comprehension of the invention and should not be construed to limit the scope thereof.

We claim:

1. A bougie for use in performing a gastroplasty, the bougie comprising:
   an elongate body having a segment configured to enter a stomach of a patient,
   the segment of the elongate body being shaped to follow a lesser curve of the stomach;
   an extension member having a distal end connected to the segment of the elongate body, the extension member being movable between:
      a retracted position in which the extension member lies along a portion of the segment of the elongate body, and
      an extended position in which the extension member extends at an angle away from the portion of the segment of the elongate body for positioning the extension member away from a gastroesophageal junction of the stomach; and
   a ring being positioned to surround the elongate body and configured to slide along the extension member to bias the extension member in at least one of:
      the extended position when the ring is placed nearby the distal end of the extension member, and
      in the retracted position when the ring is placed nearby a proximal end of the extension member.

2. The bougie of claim 1, wherein the proximal end of the extension member is a free-end that is spaced-away from the segment to define a Y-shape when the extension member is in the extended position.

3. The bougie of claim 1, further comprising at least one of:
   an extending wire being connected to the ring and configured to slide the ring in a distal direction when pulled to bias the extension member from the retracted position to the extended position, and
   a retraction wire being connected to the ring and configured to slide the ring in a proximal direction when pulled to bias the extension member from the extended position to the retracted position.

4. The bougie of claim 3, wherein the extending wire is manipulated from outside of the stomach to move the extension member to the extended position.

5. The bougie of claim 3, wherein the retraction wire is manipulated from outside of the stomach to move the extension member to the retracted position.

6. The bougie of claim 3, wherein the extending wire is a first extending wire and the bougie further comprises a second extending wire, with the first and second extending wires being similarly routed to opposite sides of the ring such that when pulled, an equal force is applied to both sides of the ring.

7. The bougie of claim 3, wherein the retraction wire is a first retraction wire and the bougie further comprises a second retraction wire, with the first and second retraction wires being similarly routed to opposite sides of the ring such that when pulled, an equal force is applied to both sides of the ring.

8. The bougie of claim 1, wherein the ring is slidable along the extension member to splay the extension member at different angles away from the elongate body and away from the gastroesophageal junction of the stomach in the extended position.

9. The bougie of claim 1, wherein the ring surrounds the portion of the segment of the elongate body when the ring is positioned nearby the distal end of the extension member to bias the extension member in the extended position.

10. The bougie of claim 1, wherein the ring surrounds both the extension member and the portion of the segment of the elongate body when the ring is positioned nearby the distal end of the extension member to bias the extension member in the extended position.

11. The bougie of claim 1, wherein the ring surrounds both the extension member and the portion of the segment of the elongate body when the ring is positioned nearby the proximal end of the extension member to bias the extension member in the retracted position.

12. The bougie of claim 1, wherein the elongated body includes a port located nearby a proximal end of the extension member to prevent the ring to slide in the proximal direction past the proximal end of the extension member.

13. The bougie of claim 1, wherein the segment of the elongate body is shaped to follow a lesser curve of the stomach.

14. The bougie of claim 1, wherein the extension member has a C-shaped cross-section.

15. A method for performing a gastroplasty using a bougie, the method comprising:
   inserting a segment of the bougie into a stomach of a patient, the bougie comprising an extension member which is in alignment with the segment of the bougie when in a retracted position during insertion;
   sliding a ring in a distal direction along the extension member to bias the extension member from the retracted position to an extended position at an angle away from the segment to establish a junction line along which opposed walls of the stomach are joinable; and
   joining the opposed walls of the stomach along the junction line and away from the gastroesophageal junction of the stomach.

16. The method of claim 15, wherein sliding the ring in the distal direction comprises adjusting a position of the ring along the extension member and away from a proximal end of the extension member to adjust the angle of the extension member in the extended position.

17. The method of claim 15, further comprising sliding the ring in a proximal direction along the extension member to bias the extension member from the extended position to the retracted position pursuant to the joining of the opposed stomach walls along the junction line.

18. The method of claim 15, wherein sliding the ring comprises pulling a wire being connected to the ring and configured to move the ring in at least one the distal direction and a proximal direction when pulled.

19. A method for performing a gastroplasty using a bougie, the method comprising:

inserting a segment of the bougie into a stomach of a patient, the bougie comprising an extension member which is in alignment with the segment of the bougie when in a retracted position during insertion;

establishing a junction line along which opposed walls of the stomach are joinable by moving the extension member of the bougie in an extended position within the stomach wherein the extension member extends at an angle away from the segment to define the junction line;

joining the opposed walls of the stomach along the junction line and away from the gastroesophageal junction of the stomach; and sliding a ring in a proximal direction along the extension member to bias the extension member from the extended position to the retracted position pursuant to the joining of the opposed stomach walls along the junction line.

20. The method of claim 19, wherein sliding the ring comprises pulling a retraction wire being connected to the ring and configured to move the ring in the proximal direction when pulled.

* * * * *